United States Patent [19]

Freudenberg

[11] Patent Number: 5,565,427

[45] Date of Patent: Oct. 15, 1996

[54] STABILIZED FACTOR VIII PREPARATIONS

[75] Inventor: Wilfried Freudenberg, Cölbe-Schönstadt, Germany

[73] Assignee: Behringwerke Aktiengesellschaft, Marburg, Germany

[21] Appl. No.: 235,241

[22] Filed: Apr. 29, 1994

Related U.S. Application Data

[63] Continuation of Ser. No. 82,911, Jun. 29, 1993, abandoned, which is a continuation of Ser. No. 864,610, Apr. 7, 1992, abandoned.

[30] Foreign Application Priority Data

Apr. 9, 1991 [DE] Germany .......................... 41 11 393.4

[51] Int. Cl.$^6$ .......................... A61K 35/14; C07K 1/00; C07K 14/00
[52] U.S. Cl. .................. 514/12; 514/21; 530/383
[58] Field of Search .................. 530/383; 514/12, 514/21

[56] References Cited

U.S. PATENT DOCUMENTS

| | | | |
|---|---|---|---|
| 4,650,858 | 3/1987 | Rasmussen et al. | 530/383 |
| 4,743,680 | 5/1988 | Mathews et al. | 530/413 |
| 5,110,907 | 5/1992 | Kosow et al. | 530/413 |

OTHER PUBLICATIONS

H. Schwinn et al., Drug. Res., vol. 39 (II.), No. 10: 1302–1305 (1989).

Meyers, R. et al., "Large Scale Preparation of a Highly Purified Solvent–Detergent Treated Factor VIII Concentrate," VOX Sang. vol. 60, pp. 141–147 (1991).

*Primary Examiner*—Elizabeth C. Weimar
*Assistant Examiner*—P. Lynn Touzeau
*Attorney, Agent, or Firm*—Finnegan, Henderson, Farabow, Garrett & Dunner, L.L.P.

[57] ABSTRACT

The invention relates to stabilized solutions with F VIII coagulation activity, to a process for the preparation thereof and to the use thereof.

13 Claims, No Drawings

STABILIZED FACTOR VIII PREPARATIONS

This application is a continuation of application Ser. No. 08/082,911 filed Jun. 29, 1993, now abandoned, which is a continuation of application Ser. No. 07/864,610, filed Apr. 7, 1992, abandoned.

The invention relates to stabilized solutions with F VIII coagulation activity, to a process for the preparation thereof and to the use thereof.

Coagulation factor VIII:C (F VIII:C) is a plasma protein and essential for the process of the intrinsic pathway of blood coagulation. A deficiency or a defect in blood coagulation factor VIII:C results in a life-threatening disturbance of blood coagulation, hemophilia A. Concentrates of F VIII:C from human plasma or genetically engineered F VIII:C are employed for the therapy of hemophilia A.

These F VIII products differ in respect of their purity, i.e. the presence of proteins which do not have coagulation activity in addition to the active substance F VIII:C. A F VIII which has more than 1000 U/mg before stabilization with albumin is called very high purity F VIII (VHP F VIII:C) (WHO, Expert Committee on Biological Standardization).

Such VHP F VIII:C have potential advantages in the treatment of hemophilia. These are the freedom from viruses and a very small content of foreign protein, which means less stress on the immune system of the patients after administration of these concentrates. The advantage which is possible per se, of less stress on the immune system of a hemophiliac patient by administration of a F VIII preparation with high specific activity, is, however, cancelled out by addition of high albumin concentrations to the highly purified product in order to stabilize the VHP F VIII. This addition of albumin means that the highly purified F VIII concentrates reach specific activities of only 3–10 U/mg in the final formulation thereof.

Although addition of albumin entails only a slight risk with respect to virus safety, it has to be borne in mind, however, that with albumin whose purity averages 95% once again unwanted concomitant proteins are administered to the patient and may stress his immune system.

High purity F VIII product: which dispense with addition of albumin for stabilization of F VIII are known (Schwinn, Smith & Wolter, Drug. Res. 39 (1989), 1302). These products reach specific activities of about 100 U/mg of protein. Based on a maximum achievable F VIII activity of about 5000 U/mg, this means that only about 2% of the protein content of these preparations comprises F VIII:C protein. It is to be assumed in this case that this 2% F VIII:C is stabilized by the 98% concomitant proteins, because a large part of these concomitant proteins is likely to comprise yon Willebrand Factor (vWF). It is known that von Willebrand Factor has a stabilizing action on F VIII:C.

The situation is different with very high purity products which have specific activities which, before albumin stabilization, are usually more than 25 times higher than for high purity products, and the vWF content thereof is very low. This low vWF content is no longer able to ensure adequate F VIII stabilization so that the F VIII activity in solutions which are not stabilized with albumin rapidly decreases.

The object of the present invention was therefore to provide a process which makes it possible to prepare a highly concentrated, physiologically tolerated solution of a VHP F VIII:C product, which solution requires no addition of proteins for stabilization.

This object is achieved according to the invention by adding an amino acid or one of its salts, derivatives or homologs to a VHP F VIII:C preparation. It is possible to add L- and/or D-amino acids. Particular suitable are arginine, lysine, ornithine, guanidinoacetic acid or others whose common feature is a basic group in the form of an amino and/or guanidino group.

The invention therefore relates to a solution with factor VIII:C activity containing an amino acid or one of its salts or derivatives and, ;here appropriate, a detergent or an organic polymer.

Preferred embodiments are:
a solution wherein the amino acid is a natural amino acid;
a solution wherein the amino acid is a basic amino acid;
a solution which contains arginine and glycine;
a solution wherein the concentration of the amino acid is 0.001 to 1 mol/l;
a solution which additionally contains an organic polymer or a nonionic detergent;
a solution wherein the F VIII:C activity derives from human factor VIII in its form which occurs in plasma or from a genetically engineered factor VIII:C or a derivative of these;
and a solution wherein the specific F VIII:C activity is at least 1000 IU/mg.

Improved stabilization is achieved by combination of amino acids or their derivatives or with a nonionic detergent such as $^R$Polysorbate 20 or $^R$Polysorbate 80 or an organic polymer such as polyethylene glycol 1500.

A combination of the amino acids arginine and glycine, preferably 0.01 to 1 mol/l, with the nonionic detergent $^R$Tween 80, preferably 0.001 to 0.5% (v/v), and with a neutral sugar such as sucrose, preferably 0.1 to 10%, has proven particularly suitable for the preparation of a stable, albumin-free VHP F VIII:C solution.

The pH of a solution of this type is adjusted to between pH 5.5 and 8.5, preferably between pH 6.5 and 7.5, by means of an organic acid, preferably 10% strength acetic acid.

The invention also relates to a pharmaceutical containing a solution of this type. Besides a solution of this type, this pharmaceutical can contain customary, pharmaceutically compatible, stabilizing and/or buffering substances, especially a carbohydrate.

The invention likewise relates to a process for the preparation of a solution of this type, wherein an amino acid or one of its salts or derivatives and, where appropriate, an organic polymer or a detergent is added to a solution with factor VIII:C activity.

The advantageous effect of the process according to the invention can be shown, for example, for a F VIII:C preparation which has been purified by chromatography on monoclonal anti-F VIII:C antibodies, it being possible for the F VIII:C to be both obtained from plasma and genetically engineered, for example in CHO (Chinese Hamster Ovary) cells. This entails, for example, equal parts of a solution of the abovementioned substances being added to the eluate from the monoclonal antibody column, and subsequently the latter being dialyzed against this solution. The stabilized F VIII:C preparation obtained in this way can be sterilized by filtration and bottled with low method-related losses. A lyophilizate of this preparation obtained in this way has unchanged high F VIII:C activities after dissolution.

It is possible with the process according to the invention to prepare a VHP F VIII:C preparation whose specific volume-based activity is at least 200 IU/ml, with a specific activity of more than 2000 IU/mg. This concentration ensures that there are no problems with manipulation owing to the need to administer small volumes.

A preparation of this type does not need further stabilization by proteins, which avoids the risk of virus contamination. At the same time, the reduction in the high protein load means a considerable reduction in the stress on the immune system of the patient due to the addition of the albumin, which is unnecessary for the medicinal action, and of the unwanted impurities contained therein.

Since physiologically tolerated substances are added for the stabilization, no intolerance reactions occur on administration of the solution according to the invention.

EXAMPLE 1

Two VHP F VIII:C preparations were prepared, both by means of affinity chromatography on monoclonal anti-vWF Ig (method of Fulcher & Zimmermann PNAS (1982), 79, 1649) and dissociation of the vWF/F VIII:C complex by solution with a $CaCl_2$ concentration of 300 mM in 0.1 M acetate, 0.1 M lysine, pH 6.8 (eluate I), and by means of chromatography on monoclonal anti-F VIII:C Ig and elution of the F VIII:C by 50% ethylene glycol in 0.1 M acetate, 0.1 M lysine, pH 6.8 (eluate II). The specific F VIII:C activity determined in eluate I was 2500 IU/mg and 419 IU/ml, and in eluate II was 3280 IU/mg and 454 IU/ml. The two eluates were divided in each case. To one portion in each case was added in the ratio 1:1 by volume a 1% strength human albumin solution in 0.75% sucrose, 3% glycine and 0.1 mol/l NaCl (eluate $I_{HSA}$, eluate $II_{HSA}$). The stabilization buffer (0.75% sucrose, 3% glycine, 3% arginine, 0.05% $^R$Tween 80, pH 6.8) was likewise added 1:1 to the other half in each case (eluate $I_S$, eluate $II_S$). The albumin-containing samples were dialyzed against 0.75% sucrose, 3% glycine, 0.1 mol/l NaCl, pH 6.8, and the others against stabilization buffer. Dialysis was carried out at 4° C. for 16 hours with 1000-fold volume change. The F VIII:C activities were measured before and after the dialysis. Table 1 shows the F VIII:C activity in % relative to the total F VIII:C activity in the particular sample before dialysis.

TABLE 1

| Eluate $I_{HSA}$ | Eluate $I_S$ | Eluate $II_{HSA}$ | Eluate $II_S$ |
| --- | --- | --- | --- |
| 92 | 94 | 94 | 93 |

The results show that stabilization of the VHP F VIII:C eluates by means of the stabilization solution according to the invention is achieved irrespective of the preparation method and to the same extent as by addition of albumin.

EXAMPLE 2

An F VIII:C eluate with a specific F VIII:C activity of 3860 IU/mg of protein and 462 IU/ml was obtained after immunoaffinity chromatography on monoclonal anti-F VIII:C antibodies. Various stabilization solutions were added to this in the ratio 1:1 by volume, and it was dialyzed against the relevant stabilization solution as described in Example 1. A pH of 6.8 was adjusted in all solutions where appropriate with 10% acetic acid.

The following stabilization solutions were employed:

I. 0.75% sucrose, 0.4 M glycine, 0.15 M sodium chloride

II. 0.01M sodium citrate, 0.08 M glycine, 0.016 M lysine, 0.0025 M calcium chloride, 0.4 M sodium chloride III. 1% sucrose, 0.14 M arginine, 0.1M sodium chloride IV. 1% sucrose, 0.4 M glycine, 0.14 M arginine, 0.1M sodium chloride, 0.05% Tween 80

The F VIII:C activity was determined before and after the dialysis. In Table 2 the F VIII:C activity after dialysis is plotted in % relative to the relevant activity before dialysis.

TABLE 2

| Mixture | I | II | III | IV |
| --- | --- | --- | --- | --- |
| F VIII:C activity after dialysis for 16 hours | 39.3% | 35.1% | 82.4% | 96.2% |

The solutions employed under I and II can be employed for the stabilization of albumin-free HP F VIII products with specific F VIII:C activities of 100–200 IU/mg, dispensing with addition of albumin. Solutions III and IV are suitable for stabilization of VHP F VIII preparations with specific F VIII:C activities greater than 1000 IU/mg.

I claim:

1. A stabilized solution with factor VIII:C activity containing factor VIII:C, an amino acid or one of its salts or homologs and a detergent or an organic polymer, wherein the specific factor VIII:C activity is at least 1000 IU/mg.

2. A solution as claimed in claim 1, wherein the amino acid is a natural amino acid.

3. A solution as claimed in claim 1, wherein the amino acid is a basic amino acid.

4. A solution as claimed in claim 1, which contains arginine and glycine.

5. A solution as claimed in claim 1, wherein the concentration of the amino acid is 0.001 to 1 mol/l.

6. A solution as claimed in claim 1, which contains an organic polymer or a nonionic detergent.

7. A solution as claimed in claim 1, wherein the F VIII:C activity is derived (a) from human factor VIII in its form which occurs in plasma or (b) from a genetically engineered factor VIII:C or (C) from a homolog of (a) or (b).

8. A pharmaceutical containing a solution as claimed in claim 1.

9. A pharmaceutical as claimed in claim 8 further containing pharmaceutically compatible, stabilizing or buffering substances.

10. A pharmaceutical as claimed in claim 9, which contains a carbohydrate.

11. A process for the preparation of a stable factor VIII:C solution which comprises adding an amino acid or one of its salts or homologs and an organic polymer or a detergent to a solution with factor VII I:C activity, wherein the specific factor VIII:C activity is at least 1000 IU/mg.

12. A stabilized solution as claimed in claim 1 containing an amino acid or one of its salts or homologs and an organic polymer, wherein the amino acid is arginine or glycine and the organic polymer is polyethylene glycol.

13. A stabilized solution as claimed in claim 1 containing an amino acid or one of its salts or homologs and a detergent, wherein the amino acid is arginine or glycine and the detergent is polyoxyethylene sorbitan mono-oleate.

* * * * *

UNITED STATES PATENT AND TRADEMARK OFFICE
CERTIFICATE OF CORRECTION

PATENT NO. : 5,565,427
DATED : October 15, 1996
INVENTOR(S) : Dr. Wilfried FREUDENBERG It is certified that error appears in the above-indentified patent and that said Letters Patent is hereby corrected as shown below:

Claim 7, column 4, line 41, "(C)" should read --(c)--.

Claim 9, column 4, line 44, after "claim 8", insert --,--.

Claim 11, column 4, line 52, "VII I:C" should read --VIII:C--.

Signed and Sealed this

Eighteenth Day of February, 1997

Attest:

BRUCE LEHMAN

Attesting Officer     Commissioner of Patents and Trademarks

(12) REEXAMINATION CERTIFICATE (4618th)
United States Patent
Freudenberg

(10) Number: US 5,565,427 C1
(45) Certificate Issued: Jul. 23, 2002

(54) STABILIZED FACTOR VIII PREPARATIONS

(75) Inventor: Wilfried Freudenberg, Cölbe-Schönstadt (DE)

(73) Assignee: Aventis Behring GmbH, Marburg (DE)

Reexamination Request:
No. 90/006,025, May 30, 2001

Reexamination Certificate for:
Patent No.: 5,565,427
Issued: Oct. 15, 1996
Appl. No.: 08/235,241
Filed: Apr. 29, 1994

Certificate of Correction issued Feb. 18, 1997.

Related U.S. Application Data

(63) Continuation of application No. 08/082,911, filed on Jun. 29, 1993, now abandoned, which is a continuation of application No. 07/864,610, filed on Apr. 7, 1992, now abandoned.

(30) Foreign Application Priority Data

Apr. 9, 1991 (DE) ............................................ 41 11 393

(51) Int. Cl.$^7$ ............................ A61K 35/14; C07K 1/00; C07K 14/00
(52) U.S. Cl. ............................. 514/12; 514/21; 530/383
(58) Field of Search ................... 514/12, 21; 530/383

(56) References Cited

U.S. PATENT DOCUMENTS

| | | | | |
|---|---|---|---|---|
| 4,440,679 A | * | 4/1984 | Fernandes et al. | 530/363 |
| 4,446,134 A | * | 5/1984 | Naito et al. | 514/2 |
| 4,495,175 A | * | 1/1985 | Chavin et al. | 530/383 |
| 4,543,210 A | * | 9/1985 | Mitra et al. | 530/383 |
| 4,623,717 A | * | 11/1986 | Fernandes et al. | 530/380 |
| 4,650,858 A | * | 3/1987 | Rasmussen et al. | 530/383 |
| 4,743,680 A | * | 5/1988 | Mathews et al. | 530/383 |
| 4,749,780 A | * | 6/1988 | Andersson et al. | 530/383 |
| 4,795,806 A | * | 1/1989 | Brown et al. | 530/383 |
| 4,857,635 A | * | 8/1989 | Zimmerman et al. | 530/383 |
| 4,877,608 A | * | 10/1989 | Lee et al. | 424/85.8 |
| 5,110,907 A | * | 5/1992 | Kosow et al. | 530/383 |
| 5,328,694 A | * | 7/1994 | Schwinn | 424/423 |
| 5,565,427 A | * | 10/1996 | Freudenberg | 514/12 |
| 5,605,884 A | * | 2/1997 | Lee et al. | 514/8 |
| 5,760,183 A | * | 6/1998 | Dazey et al. | 530/383 |

FOREIGN PATENT DOCUMENTS

| | | | |
|---|---|---|---|
| AU | 60150/90 | * | 2/1991 |
| EP | 123 945 | * | 11/1984 |
| EP | 315 968 | * | 5/1989 |
| EP | 383 645 | * | 8/1990 |
| EP | 468 181 | * | 1/1992 |
| GB | 941019 | * | 11/1963 |
| WO | 91/10439 | * | 7/1991 |

OTHER PUBLICATIONS

Myers et al. Large–Scale Preparation of a Highly Purified Solvent–Detergent Treated Factor VIII Concentrate. Vox Sang. 1991, vol. 60, pp. 141–147.*

Fay et al. Purification and characterization of a highly purified human factor VIII consisting of a single type of polypeptide chain. Proc. Natl. Acad. Sci. USA. Dec. 1982, vol. 79, pp. 7200–7204.*

Fulcher et al. Characterization of the human factor VIII procoagulant protein with a heterologous precipitating antibody. Proc. Natl. Acad. Sci. USA. Mar. 1982, vol. 79, pp. 1648–1652.*

Schwinn et al. Progress in Purification of Virus–inactivated Factor VIII Concentrates. Drug Res. 1989, vol. 39 (II), No. 10, pp. 1302–1305.*

Lewis, Sr. Hawley's Condensed Chemical Dictionary, Twelfth Edition. 1993, pp. 53, 357, 606, 936, 1020.*

* cited by examiner

*Primary Examiner*—Jeffrey E. Russel

(57) ABSTRACT

The invention relates to stabilized solutions with F VIII coagulation activity, to a process for the preparation thereof and to the use thereof.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–13 is confirmed.

* * * * *

(12) EX PARTE REEXAMINATION CERTIFICATE (5561st)
United States Patent
Freudenberg

(10) Number: US 5,565,427 C2
(45) Certificate Issued: Oct. 10, 2006

(54) STABILIZED FACTOR VIII PREPARATIONS

(75) Inventor: Wilfried Freudenberg, Cölbe-Schönstadt (DE)

(73) Assignee: A. Nattermann und Cie GmbH, Cologne (DE)

Reexamination Request:
No. 90/006,823, Oct. 21, 2003

Reexamination Certificate for:
Patent No.: 5,565,427
Issued: Oct. 15, 1996
Appl. No.: 08/235,241
Filed: Apr. 29, 1994

Reexamination Certificate C1 5,565,427 issued Jul. 23, 2002

Certificate of Correction issued Feb. 18, 1997.

Related U.S. Application Data

(63) Continuation of application No. 08/082,911, filed on Jun. 29, 1993, now abandoned, which is a continuation of application No. 07/864,610, filed on Apr. 7, 1992, now abandoned.

(30) Foreign Application Priority Data

Apr. 9, 1991 (DE) .......................................... 41 11 393

(51) Int. Cl.
*A61K 35/14* (2006.01)
*C07K 1/00* (2006.01)
*C07K 14/00* (2006.01)

(52) U.S. Cl. ............................. 514/12; 514/21; 530/383
(58) Field of Classification Search .................... 514/12, 514/21; 530/383
See application file for complete search history.

(56) References Cited

U.S. PATENT DOCUMENTS

| | | | |
|---|---|---|---|
| 4,089,944 A | 5/1978 | Thomas | 424/101 |
| 4,297,344 A | 10/1981 | Schwinn et al. | 424/101 |
| 4,614,795 A | 9/1986 | Chavin et al. | 530/383 |
| 4,758,657 A | 7/1988 | Farb et al. | 530/383 |
| 4,981,951 A | 1/1991 | Tsay | 530/383 |
| 5,043,428 A | 8/1991 | Heimburger et al. | 530/383 |
| 5,068,106 A | 11/1991 | Pâques et al. | 424/94.3 |
| 5,424,401 A | 6/1995 | Heimburger et al. | 530/383 |

FOREIGN PATENT DOCUMENTS

| | | | |
|---|---|---|---|
| EP | 0 035 204 B1 | | 9/1981 |
| EP | 0 286 323 B1 | | 10/1988 |
| EP | 0 314 095 | | 5/1989 |
| EP | 0 412 466 A2 | | 8/1990 |
| EP | 0 410 207 | * | 1/1991 |
| WO | WO 90/05140 | | 5/1990 |

OTHER PUBLICATIONS

Oct. 4, 2004, Deposition Transcript and Exhibits of the Deposition of C. Einaudi.
Oct. 12, 2004, Deposition Transcript and Exhibits of the Deposition of J. Bennett.
Oct. 14, 2004, Deposition Transcript and Exhibits of the Deposition of H. Lauppe.
Oct. 15, 2004, Deposition Transcript and Exhibits of the Deposition of A. Groner.
Oct. 21, 2004, Deposition Transcript and Exhibits of the Deposition of W. Freudenberg.
Feb. 15, 2004, Letter to Judge Brody with exhibits.
Jul. 11, 2003, Transcript of Jul. 11, 2003 hearing.
Jul. 30, 2003, Plaintiffs' Response to Baxter's First Set of Interrogatories (Nos. 1–16) and Notice of Service.
Aug. 13, 2003, Plaintiffs' Objections and Responses to Baxter's First Set of Requests for Admission (Nos. 1–85) and Notice of Service.
Sep. 17, 2003, Highlighted Farb document submitted during the Sep. 17, 2003 hearing with Judge Sleet.
Sep. 17, 2003, Transcript of Sep. 17, 2003 hearing.
Oct. 1, 2003, Plaintiffs' Supplemental Response to Baxter's First Set of Interrogatories (Nos. 1–16) and Notice of Service.
Oct. 7, 2003, Letter from Balick to Judge Sleet.
Oct. 7, 2003, Letter from Rovner to Judge Sleet.
Oct. 10, 2003, Transcript of Oct. 10, 2003 hearing.
Jul. 30, 2003, Plaintiffs' Objections and Responses to Bayer's First Set of Interrogatories (Nos. 1–19) and Verification of Answers and Certificate of Service.
Aug. 4, 2003, Defendants' Responses to Plaintiffs' First Set of Interrogatories (Nos. 1–18) and Certificate of Service.
Aug. 4, 2003, Defendants' Responses to Plaintiffs' First Set of Requests for Admission (Nos. 1–13) and Certificate of Service.
Oct. 3, 2003, Plaintiffs' Objections and Responses to Bayer's First Set of Requests for Admission (Nos. 1–8) and Notice of Service.
Oct. 3, 2003, Plaintiffs' Objections and Responses to Bayer's Second Set of Interrogatories (Nos. 20–26) and Notice of Service.
Nov. 12, 2003, Plaintiffs' Motion to Dismiss All Claims and Counterclaims without Prejudice or, in the Alternative, Stay Proceedings Pending Reexamination of U.S. Pat. No. 5,565,427.
Nov. 21, 2003, Plaintiff's Opposition to Defendant's Motion for leave to file amended answer and counterclaims.
Mar. 22, 2004, Transcript of Motion before Judge Brody to stay or dismiss.
Mar. 30, 2004, ORDER.
Mar. 30, 2004, Bayer's subpoena of Finnegan–Henderson of documents in attached Schedule A.
Mar. 30, 2004, Defendant's Revised Notice of Deposition of A. Nattermann & Cie GmbH, Aventis Behring L.L.C. & Aventis Behring GmbH Pursuant to Rule 30(b)(6).
Apr. 2, 2004, Notice of Service of Subpoena on Finnegan–Henderson and Subpoena itself.

(Continued)

*Primary Examiner*—Kathleen M. Kerr

(57) ABSTRACT

The invention relates to stabilized solutions with F VIII coagulation activity, to a process for the preparation thereof and to the use thereof.

OTHER PUBLICATIONS

May 3, 2004, Letter from T. Donaldson to T. Poche attaching Plaintiffs' objections and responses to Bayer's Mar. 30, 2004 Subpoena of Finnegan Henderson.
May 8, 2004, Order of May 8, 2004.
May 13, 2004, Order that Defendants' motion for summary judgment is DENIED without prejudice.
Jun. 1, 2004, ORDER memorializing parties agreement to complete depositions on or before Oct. 15, 2004.
Jun. 4, 2004, ORDER stating that Plaintiff's Motion to Stay and Plaintiff's Motion for Discovery are Denied as moot.
Sep. 27, 2004, Letter attaching copies of Subpoena of D. Farb, Notice of Services of Subpoena, Defendants' Notice of Deposition of Farb.
Sep. 27, 2004, Letter stating that Finnegan will be representing Dr. D. Farb at his deposition and will accept service on his behalf.
Sep. 28, 2004, Letter from T. Donaldson to T. Poche.
Oct. 21, 2004, Transcript of teleconference between Bayer, Aventis and Judge Brody re deposition of Dr. Freudenberg.
Feb. 16, 2005, Letter to Judge Brody.
Feb. 24, 2005, Letter to Judge Brody.
Mar. 4, 2005, Letter to the Court.
Mar. 10, 2005, Letter to the Court.
Mar. 11, 2005, Letter to Judge Brody.
Mar. 15, 2005, Letter to Judge Brody.
Mar. 16, 2005, Letter to Judge Brody.
Mar. 16, 2005, Copy of ORDER maintaining current stay pending the reexamination by the USPTO and requiring that parties keep the Court updated on its progress.
Derwent Abstract for WO 90/05140.
I. Scharrer, "Current status of a recombinant antihemophilic factor VIII clinical trial organized by Baxter," *Ann. Hematology*, 63: 172–176 (1991).
Order Granting Plaintiff's Motion for Discovery Under FED. R. CIV. P. 56(f).
Motion for Discovery Under FED. R. CIV. P. 56(f) on behalf of Plaintiffs filed Nov. 24, 2003.
Redacted Copy of Plaintiff's Memorandum in Support of Motion for Discovery Under FED. R. CIV. P. 56(f) filed Nov. 24, 2003, with attached Exhibits 1–16.
Order Denying Bayer's Motion for Summary Judgment of Noninfringement.
Redacted copy of Plaintiff's Opposition to Defendant's Motion for Summary Judgment of Noninfringement filed Nov. 24, 2003, with attached Exhibits 1–9.
Order Dismissing All Claims and Counterclaims Without Prejudice.
Order Staying Any Further Proceedings Pending Outcome of Reexamination of U.S. Pat. No. 5,565,427.
Plaintiffs' Memorandum of Law in Support of Its Motion to Dismiss All Claims and Counterclaims Without Prejudice or, in the Alternative, Stay Proceedings Pending Reexamination of U.S. Pat. No. 5,565,427 (Exhibits 1–10) filed Jan. 16, 2004.
Plaintiff's Answer to First Amended Counterclaims, filed Dec. 23, 2003.
Transcript of Dec. 1, 2003, hearing before the Honorable Anita B. Brody in Civil Action No. 03–2268 in the United States District Court for the Eastern District of Pennsylvania.
Bayer's Opposition to Plaintiffs' Motion to Dismiss All Claims and Counterclaims Without Prejudice or, in the Alternative, Stay Proceedings Pending Reexamination of U.S. Pat. No. 5,565,427 (with Exhibits), filed Jan. 30, 2004.
Plaintiffs' Memorandum of Law in Opposition to Defendants' Motion For a Rule 54(b) Declaratory Judgment Regarding Aventis Behring's State Court Action (with Exhibits), filed Feb. 9, 2004.
Plaintiffs' Reply Memorandum of Law in Support of its Motion to Dismiss All Claims and Counterclaims Without Prejudice or, in the Alternative, Stay Proceedings Pending Reexamination of U.S. Pat. No. 5,565,427 (with Exhibits), filed Feb. 13, 2004.
Defendants' Reply to Plaintiffs' Memorandum of Law in Opposition to Defendants' Motion For Rule 54(b) Declaratory Judgment Regarding Aventis Behring's State Court Action (with Exhibits), filed Feb. 16, 2003.
Order dated Feb. 19, 2004 in Civ. A. No. 03–2268 (*Nattermann v. Bayer* litigation).
Letter from Bayer's counsel to Honorable Anita B. Brody regarding Protective Order (with Exhibits) dated Mar. 12, 2004.
Letter from Nattermann's counsel to Honorable Anita B. Brody regarding Protective Order dated Mar. 17, 2004.
Order dated Nov. 25, 2003 in Civ. A. No. 03–2268 (*Nattermann v. Bayer* litigation).
Bayer's Opposition to Plaintiffs' Motion To Dismiss All Claims And Counterclaims Without Prejudice or, in the Alternative, Stay Proceedings Pending Reexamination (with Exhibits), filed Nov. 26, 2003.
Defendants' First Amended Answer And Counterclaims, filed Nov. 26, 2003.
Transcript of Hearing Held on Dec. 1, 2003 in Civ. A. No. 03–2268 (*Nattermann v. Bayer* Litigation).
Plaintiffs' Answer to First Amended Counterclaim, filed Dec. 23, 2003.
Letter from Bayer's Counsel to Honoroable Anita B. Brody dated Jan. 7, 2004, submitted in Civ. A. No. 03–2268 (with Exhibits).
Letter from Nattermann's counsel to Honorable Anita B. Brody dated Jan. 9, 2004, submitted in Civ. A. No. 03–2268 (with Exhibits).
Plaintiffs' Motion To Dismiss All Claims And Counterclaims Without Prejudice Or, In The Alternative, Stay Proceedings Pending Reexamination Of U.S. Pat. No. 5,565,527 (with Order and Exhibits), filed Jan. 16, 2004.
Letter from Bayer's counsel to Honorable Anita B. Brody forwarding Stipulated Protective Order and copy of Stipulated Protective Order, dated Jan. 21, 2004.
Transcript of Jan. 12, 2004 hearing in the Civ. A. No. 03–2268 (*Nattermann v. Bayer* litigation).
Bayer's Motion For Declaratory Judgment of Waiver of Plaintiff's Compulsory Counterclaims (with Exhibits), filed Jan. 26, 2004.
Order dated Jan. 29, 2004 in Civ. A. No. 03–2268 (*Nattermann v. Bayer* litigation).
Arakawa, Tsutomu et al., "Stabilization of Protein Structure by Sugars," Biochemistry, vol. 21: 6536–6544 (1982).
Berntorp, Erik, et al., "Hepatitis C Virus Transmission by Monoclonal Antibody Purified Factor VIII Concentrate," The Lancet, vol. 335: 1531–1532 (1990).
Bray, Gordon L., "Recent Advances in the Preparation of Plasma–Derived and Recombinant Coagulation Factor VIII," The Journal of Pediatrics: 503–507 (1990).

Tootill, E., "The Facts on File Dictionary of Biology," Revised and Expanded Edition, pp. 44; 293.

Kernoff, Peter B. A., "Hepatitis and Factor VIII Concentrates," Seminars in Hematology, vol. 25:2, Suppl. 1: 8–13 (1988).

Lee, James C. et al., "The Stabilization of Proteins by Sucrose," The Journal of Biological Chemistry, vol. 256: (14) 7193–7201 (1981).

Lusher, Jeanne M. et al., "Viral Safety and Inhibitor Development Associated With Factor VIIIC Ultra–Purified From Plasma in Hemophiliacs Previously Unexposed to Factor VIIIC Concentrates," Seminar in Hematology, vol. 27:2, Suppl. 2: 1–7 (1990).

Budavari, Susan et al. (eds.), "The Merck Index, An Encyclopedia of Chemicals, Drugs, and Biologicals," p. 1401 (1989).

Pierce, Glen F. et al., "The Use of Purified Clotting Factor Concentrates in Hemophilia, Influence of Viral Safety, Cost, and Supply on Therapy," JAMA, vol. 261:23, (1989).

Stryer, Lubert, "Biochemistry Third Edition," pp. 16–21 (1988).

A. Munoz et al., "A randomized hemodynamic comparison of intravenous amiodarone with and without Tween 80," *European Heart Journal*, vol. 9: 142–148 (1988).

Complaint for Patent Infringement filed by A. Nattermann & Cie GmbH et al. against Baxter Healthcare Corp. in the District Court for the District of Delaware (Apr. 11, 2003).

Answer and Counterclaim for Declaratory Judgment filed by Baxter Healthcare Corp. in the District Court for the District of Delaware (May 27, 2003).

Reply of Counterclaim filed by A. Nattermann & Cie GmbH et al. in the District Court for the District of Delaware (Jun. 18, 2003).

Defendants' Answer and Counterclaims filed by Bayer Corp. et al., in the District Court for the Eastern District of Pennsylvania (May 1, 2003).

Answer to Counterclaims filed by A. Nattermann & Cie GmbH et al. in the District Court for the Eastern District of Pennsylvania (May 21, 2003).

Defendants' Motion for Summary Judgment of Noninfringement (with attachments), filed by Bayer Corp. et al., in the District Court for the Eastern District of Pennsylvania (Oct. 10, 2003).

Memorandum in Support of Defendants' Motion for Summary Judgment of Noninfringement (with attachments), filed by Bayer Corp. et al., in the District Court for the Eastern District of Pennsylvania (Oct. 10, 2003).

Bayer Corporations's and Bayer Healthcare LLC's Motion for Leave to File Defendants' First Amended Answer and Counterclaims filed in the District Court for the Eastern District of Pennsylvania (with attachments) (Oct. 14, 2003).

Bayer Corporations's and Bayer Healthcare LLC's Memorandum in Support of Their Motion for Leave to File Defendants' First Amended Answer and Counterclaims filed in the District Court for the Eastern District of Pennsylvania (with attachments) (Oct. 14, 2003).

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 11 is confirmed.

Claim 1 is cancelled.

Claims 2–8, 10, 12 and 13 are determined to be patentable as amended.

Claim 9, dependent on an amended claim, is determined to be patentable.

New claims 14–23 are added and determined to be patentable.

2. A solution as claimed in claim [1] *15*, wherein the amino acid is a natural amino acid.

3. A solution as claimed in claim [1] *15*, wherein the amino acid is a basic amino acid.

4. A *stabilized* solution [as claimed in claim 1, which] *with factor VIII:C activity containing factor VIII:C, an amino acid or one of its salts or homologs and a detergent or an organic polymer, wherein the specific factor VIII:C activity is at least 1000 IU/mg and wherein the stabilized solution* contains arginine and glycine.

5. A solution as claimed in claim [1] *15*, wherein the concentration of the amino acid is 0.001 to 1 mol/l.

6. A solution as claimed in claim [1] *15*, which contains an organic polymer or a nonionic detergent.

7. A solution as claimed in claim [1] *15*, wherein the F VIII:C activity is derived (a) from human factor VIII in its form which occurs in plasma or (b) from a genetically engineered factor VIII:C or (c) from a homolog of (a) or (b).

8. A pharmaceutical containing a solution as claimed in claim [1] *14*.

10. A pharmaceutical [as claimed in claim 9,] which contains *a stabilized solution with factor VIII:C activity containing factor VIII:C, an amino acid or one of its salts or homologs, a detergent or an organic polymer, and* a carbohydrate *wherein the specific factor VIII:C activity is at least 1000 IU/mg, and further containing pharmaceutically compatible, stabilizing or buffering substances*.

12. A stabilized solution [as claimed in claim 1] *with factor VIII:C activity* containing *factor VIII:C, an* amino acid or one of its salts or homologs and an organic polymer, *wherein the specific factor VIII:C activity is at least 1000 IU/mg, and wherein the amino acid is arginine or glycine and the organic polymer is polyethylene glycol.*

13. A stabilized solution as claimed in claim [1] *15*, containing an amino acid or one of its salts or homologs and a detergent, wherein the amino acid is arginine or glycine and the organic detergent is polyoxyethylene sorbitan monooleate.

*14. A stabilized solution with factor VIII:C activity containing factor VIII:C, an amino acid or one of its salts or homologs and a detergent or organic polymer, wherein the specific factor VIII:C activity is at least 2000 IU/mg.*

*15. A stabilized solution with factor VIII:C activity containing factor VIII:C, an amino acid or one of its salts or homologs, a detergent or organic polymer, and a carbohydrate, wherein the specific factor VIII:C activity is at least 1000 IU/mg.*

*16. A stabilized solution with factor VIII:C activity containing factor VIII:C, an amino acid or one of its salts or homologs, a detergent or organic polymer, and a carbohydrate, wherein the specific factor VIII:C activity is at least 2000 IU/mg.*

*17. A stabilized solution with factor VIII:C activity containing factor VIII:C, an amino acid or one of its salts or homologs, a detergent or organic polymer, and a carbohydrate, wherein the specific factor VIII:C activity is at least 3280 IU/mg.*

*18. A stabilized solution with factor VIII:C activity containing factor VIII:C, an amino acid or one of its salts or homologs, a detergent or organic polymer, and a carbohydrate, wherein the specific factor VIII:C activity is at least 2000 IU/mg and wherein the stabilized solution with factor VIII:C activity does not contain albumin.*

*19. A stabilized solution with factor VIII:C activity containing factor VIII:C, an amino acid or one of its salts or homologs, a detergent or organic polymer, and a carbohydrate, wherein after lyophilization and reconstitution, the specific factor VIII:C activity is at least 2000 IU/mg.*

*20. A solution as claimed in claim 7, wherein the factor VIII:C activity is derived from a genetically engineered factor VIII:C.*

*21. A stabilized solution with factor VIII:C activity containing factor VIII:C, an amino acid or one of its salts or homologs, a detergent or organic polymer, wherein the specific factor VIII:C activity is at least 1000 IU/mg and wherein the potency of the stabilized factor VIII:C solution is at least 200 IU/ml.*

*22. A stabilized solution with factor VIII:C activity containing factor VIII:C, an amino acid or one of its salts or homologs, a detergent or organic polymer, and a carbohydrate, wherein the specific factor VIII:C activity is at least 2000 IU/mg and wherein the potency of the stabilized factor VIII:C solution is at least 200 IU/ml.*

*23. A stabilized solution with factor VIII:C activity containing factor VIII:C, an amino acid or one of its salts or homologs and a detergent or an organic polymer, wherein the specific factor VIII:C activity is at least 1000 IU/mg and wherein the concentration of detergent is from 0.001 to 0.05% v/v.*

\* \* \* \* \*